United States Patent [19]

Bakker et al.

[11] Patent Number: 5,147,401
[45] Date of Patent: Sep. 15, 1992

[54] ARTIFICIAL SKIN

[75] Inventors: Dirkjan Bakker, Alphen Aan Den Rijn; Maria Ponec-Waelsch, Leiderdorp, both of Netherlands

[73] Assignee: H.C. Implants B.V., Leiden, Netherlands

[21] Appl. No.: 574,659

[22] Filed: Aug. 29, 1990

[30] Foreign Application Priority Data

Sep. 6, 1989 [NL] Netherlands .......................... 8902237

[51] Int. Cl.$^5$ .......................... A61F 2/10; A61F 13/00; A61F 15/00; B32B 3/26
[52] U.S. Cl. ....................... 623/15; 602/41; 428/304.4
[58] Field of Search ....................... 623/15, 1; 128/155, 128/82, 156; 428/304.4, 319.3, 319.7; 604/366

[56] References Cited

U.S. PATENT DOCUMENTS

| | | |
|---|---|---|
| 3,908,201 | 9/1975 | Jones et al. |
| 4,553,272 | 11/1985 | Mears . |
| 4,685,455 | 8/1987 | Vrouenraets .......................... 128/155 |
| 4,985,036 | 1/1991 | Lommen et al. .......................... 623/15 |

FOREIGN PATENT DOCUMENTS 2170713A 2/1985 United Kingdom .

Primary Examiner—Randall L. Green
Assistant Examiner—Dinh X. Nguyen
Attorney, Agent, or Firm—Bachman & LaPointe

[57] ABSTRACT

The invention relates to an artificial skin which is made up of (1) a water vapor-permeable, non-porous top layer of a segmented thermoplastic copolyester with a thickness of 5-200 μm, consisting essentially of a multiplicity of recurring long-chain-ester-units and short-chain-ester-units, the long-chain-ester-units making up 30-70% by weight of the copolyester and being represented by the formula

—OLO—CO—R—CO— and the short-chain-ester-units being represented by the formula

—OEO—CO—R—CO— wherein
L in the long-chain-unit represents a divalent group which remains after removal of the terminal hydroxyl groups from a poly(oxyethylene) glycol with an average molecular weight of 500-3000;
R is a divalent group which remains after removing the carboxyl groups from a dicarboxylic acid with a molecular weight of at most 300; and
E in the abovementioned short-chain-unit represents an alkylene group having 2-6 carbon atoms, and (2) a macroporous underlayer of a degradable, biocompatible (co)polymer having a thickness of 30-300 μm, the diameter of the pores having a value of 30-300 microns and the macroporosity being 30-80%.

The artificial skin according to the invention can also be designed as a single-layer film, in which case the abovementioned top layer and underlayer gradually merge into one another. Furthermore, the top layer of the artificial skin can be provided with autologous epithelial cells such as keratinocytes and the underlayer can be provided with autologous fibroblasts.

12 Claims, 1 Drawing Sheet

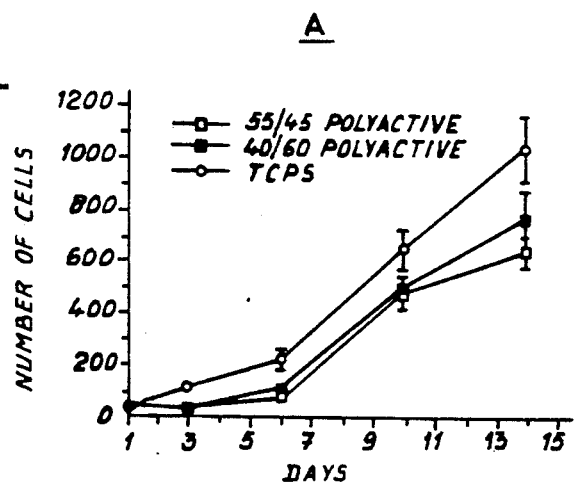
Fig-1
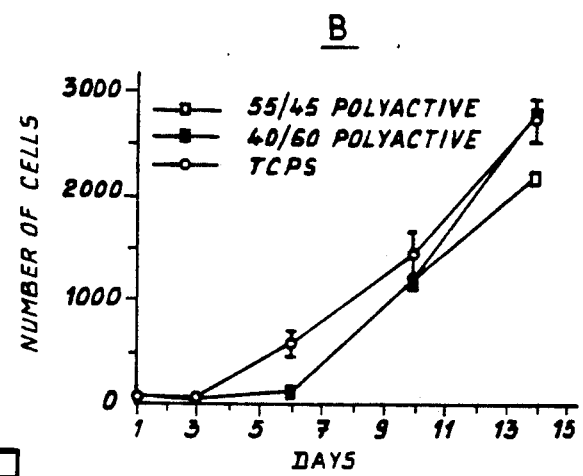
Fig-2
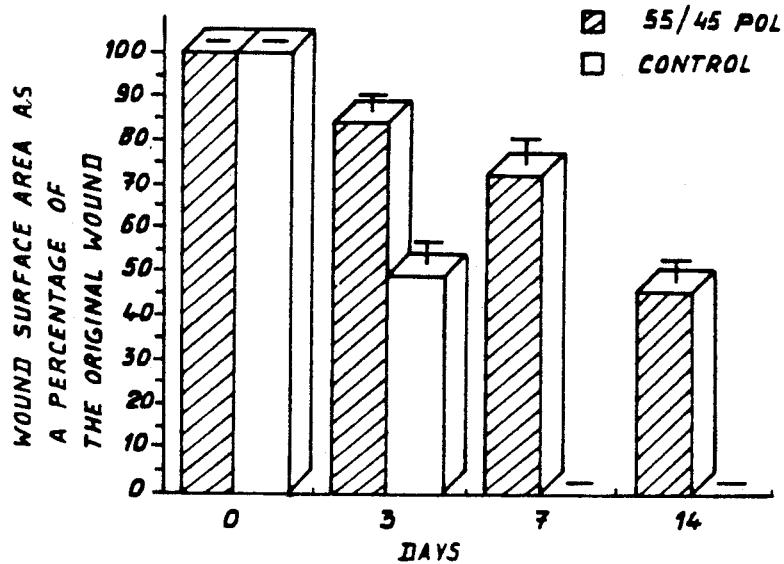

ARTIFICIAL SKIN

The invention relates to an artificial skin or wound-covering material which can be used externally on, in particular, deep wounds such as burns and the like.

As is known, human skin forms a barrier against adverse external influences such as infections. If part of the skin is damaged, as, for example, in the case of burns, complications usually arise since, on the one hand, the protective function of the skin has been lost and therefore a microbial invasion will take place and, on the other hand, a substantial moisture loss will occur.

The Applicant has therefore carried out research for an artificial skin which is able to take over all or a large part of the function of the natural skin during the period that the wound is still not covered by an epidermis and dermis, and which artificial skin will also be able to serve as carrier material for cultured autologous keratinocytes, which will have a favourable influence on the recovery of the epidermis. An artificial skin of this type must, however, satisfy diverse requirements. As stated, an artificial skin of this type must, for example, on the one hand be closed to bacteria and the like and restrict substantial moisture loss while, on the other hand, it must be possible for adequate water vapour transport to take place through the artificial skin, during which transport nutrients from the underlying tissue are able to make their way to the recovering skin in sufficient quantity. At the same time, the artificial skin must adhere to the underlying wound bed immediately after its application and a permanent adhesion must form as a result of ingrowth of tissue. The side of the artificial skin which is resting on the wound bed must therefore be porous so that ingrowth of tissue is possible. If appropriate, fibroblasts can be cultured in the porous lower layer of the artificial skin before covering the wound. As reminded above, an artificial skin of this type can also serve as carrier material for cultured autologous keratinocytes (which form a fragile cellular layer during culture) and must therefore be able to be handled adequately to enable the culture/carrier material combination to be applied to the wound bed. Because the artificial skin serves as a carrier for cultured cells, the gradual degradation thereof is seen as an advantage.

An artificial skin which meets the abovementioned requirements has been found which is made up of (1) a water vapour-permeable, non-porous top layer of a segmented thermoplastic copolyester, consisting essentially of a multiplicity of recurring long-chain-ester-units and short-chain-ester-units, the long-chain-ester-units making up 30–70% by weight of the copolyester and being represented by the formula

and the short-chain-ester-units being represented by the formula

wherein

L in the long-chain-unit represents a divalent group which remains after removal of the terminal hydroxyl groups from a poly(oxyethylene) glycol with an average molecular weight of 500–3000;

R is a divalent group which remains after removing the carboxyl groups from a dicarboxylic acid with a molecular weight of at most 300; and E in the abovementioned short-chain-unit represents an alkylene group having 2–6 carbon atoms, having a thickness of 5–200 μm, and (2) a macroporous lower layer of a degradable, biocompatible (co)-polymer having a thickness of 30–300 μm, the diameter of the macropores having a value in the range from 30–300 microns and the macroporosity being 30–80%. The term "macroporosity" is understood to mean the volume of macropores per unit volume multiplied by a factor of 100.

It is also possible according to the invention to spread a single-layer film (porous film) of an above-defined segmented thermoplastic copolyester in a generally known manner in such a way that one of the sides is virtually closed and the other side is fairly open. In the case of a single-layer film the abovementioned term " . . . non-porous top layer" namely also includes the possibility that one side of the single-layer film has a macroporosity which is at most 10% and advantageously 5% or less of the macroporosity of the other (macroporous) side of the single-layer film. Specifically in combination with the culture of keratinocytes on the denser side, an artificial skin is obtained which is sufficiently occlusive, comparable with the abovementioned double-layer structure (that is to say the films with the closed top layer and the porous underlayer). The macroporosity of these single-layer films is between 30–80%, the film thickness between 100 and 300 microns and the pore diameter between 30 and 250 microns.

More particularly, the top layer of the artificial skin according to the invention is produced from the above-defined thermoplastic copolymers, in which the poly-(oxyethylene) glycol units L have a molecular weight of approximately 750–1500 and in particular of approximately 1000. Furthermore, the symbol E preferably represents a 1,2-ethylene group or 1,4-butylene group, that is to say the short-chain-ester-units are preferably based on either poly(1,2-ethylene terephthalate) or poly(1,4-butylene terephthalate). Furthermore, the symbol R is advantageously essentially derived from terephthalic acid. The molecular weight of such copolymers is usually $(30-150) \cdot 10^3$. For example, the 55 PEO/45 PBT used within the framework of the invention has a molecular weight of 80,000.

The material from which the top layer of the artificial skin according to the invention is produced is to a greater or lesser extent known from the prior art. For example, copolymers of poly(ethylene glycol) and bis(-beta-hydroxyethyl) terephthalate are mentioned in the examples of U.S. Pat. No. 3,908,201. The average molecular weight of the poly(ethylene glycol) units preferably used was approximately 4,000. This molecular weight of 4,000 agrees with the preferably used value for the $CH_2$—$CH_2$—O units, as stated in column 7, line 2 of said U.S. patent. Furthermore, U.S. Pat. No. 3,908,201 also mentions a copolymer which is made up of 50% by weight of units which are derived from poly(ethylene glycol) with an average molecular weight of 600 and 50% by weight of units which are derived from poly(ethylene terephthalate).

(Co)polymers which can be used as the degradable, biocompatible (co)polymer for the underlayer of the artificial skin according to the invention are the (co)polymers considered acceptable in the medical sector, such as, for example, poly-L-lactic acid with an average molecular weight of (5–100) $10^4$ and also poly-D-lactic acid, polyglycolic acid and the above-defined thermoplastic copolyesters, from which the top layer of the artificial skin in question is made up. Advantageously, the top layer and the underlayer of the artificial skin according to the invention are made up of the same material, such as, for example, polyoxyethylene-/polybutylene terephthalate materials (PEO/PBT). More particularly, PEO/PBT materials of this type are obtainable as a commercial product under the provisional tradename "Polyactive" (Holland Composite Implants B.V., The Netherlands).

As stated above, single-layer films can also be used. Single-layer films produced by the Applicant were made up of PEO/PBT materials and designated "Polyactive", that is to say 40 PEO/60 PBT, 55 PEO/45 PBT and 60 PEO/40 PBT.

One of the important advantages of the abovementioned PEO/PBT copolymers lies in the fact that these materials are very suitable as a substrate for culturing epithelial cells such as keratinocytes. It is also possible to culture fibroblasts on such PEO/PBT materials and these materials can therefore likewise advantageously be used as the porous underlayer for the artificial skin according to the invention. The latter also applies in the case of the abovementioned poly-L-lactic acid. Furthermore, it is pointed out in this context that a possible delay in the initial cell growth on the abovementioned materials can be overcome by improving the cell adhesion with aid of, inter alia, laminin, collagen (type IV), proteoglycans or fibronectin, which is applied by (pre)-coating to the surface of the material which is to be covered. It is further possible to obtain this purpose (improvement of the initial cell growth) by modification of the surface of the above materials, for instance by a plasma or a glow discharge treatment, radiation, monomer grafting or hydrolytic etching (with sulphuric acid e.g.)

The invention therefore also relates to the therapeutic use of the above-defined artificial skin or wound-covering material, it being possible for the non-porous top layer of the artificial skin to be provided with autologous epithelial cells such as autologous keratinocytes and for the macroporous underlayer of the artificial skin according to the invention to be provided with autologous fibroblasts.

The invention is illustrated with reference to the examples below, which must not be taken as restrictive.

EXAMPLE I

Production of artificial skin

Various artificial skins according to the invention were produced, the non-porous or closed top layer having a thickness of 5–100 μm and the macroporous underlayer having a thickness of 150–300 μm. The porosity was obtained with the aid of the generally known "salt casting" technique, with which, for example, sodium citrate or sodium chloride can be used as the salt. The pores varied from 36–212 μm. The top layer of the artificial skin according to the invention consisted either of Polyactive 55/45 (PEO/PBT) or 40/60 (PEO/PBT). The macroporous underlayer of the artificial skin consisted of the abovementioned Polyactive materials or of poly-L-lactic acid with a molecular weight of 104 kD.

Culture tests

Keratinocytes from the skin from the back of a rat and from human foreskin were cultured on the abovementioned artificial skins in accordance with the technique of Rheinwald and Green (J.G. Rheinwald, et al. Serial cultivation of strains of human epidermal keratinocytes; the formation of keratinizing colonies from single cells, Cell 6 (1975), pp. 317–330). Human foreskin fibroblasts and rat fibroblasts were also isolated and cultured in DMEM medium (Dulbecco Modification of Eagle's Medium), which was made up with 10% serum.

The morphology of these cell types on the above-described biomaterials and on "tissue culture polystyrene" (TCPS) were assessed by means of phase contrast and scanning electron microscopy. The proliferation activity of the keratinocytes on the closed films of the two Polyactive materials (55 PEO/45 PBT and 40 PEO/60 PBT) and on TCPS was determined by means of a cell count on days 1, 3, 6, 10 and 14.

The tests showed that the keratinocytes which were cultured on the closed Polyactive films first formed small colonies and grew to a confluent culture within 8 days. After confluence was achieved, multi-layer formation of the cell culture occurred as a consequence of the differentiation of the keratinocytes, which corresponds to the behaviour of the cells which were cultured on TCPS as substrate. This phenomenon occurred with keratinocytes of both human and rat origin.

Scanning electron microscopy showed that the keratinocytes occurred as flat polygonal cells in close apposition and were covered with microvilli. The shape, size and microvilli density of the keratinocytes which were cultured on the two Polyactive films were similar to the shape, size and microvilli density which were assumed in the case of keratinocytes cultured on TCPS.

The growth curves of the keratinocytes, as shown in FIG. 1 A/B, show an increasing number of cells during the entire culture period. Quantitative analysis confirmed the observation with the phase contrast microscope, namely that the initial growth of the keratinocytes on the two Polyactive materials as substrate was delayed compared with TCPS. In this respect there was no difference between keratinocytes from the skin from the back of a rat or human foreskin; the differences between the biomaterials and TCPS were not statistically significant (5% interval, both sides).

In the case of fibroblasts, which were cultured for 8 days on closed films of the Polyactive materials and poly-L-lactic acid, it was found that these formed a continuous layer and had a flat shape, which corresponds with that of fibroblasts cultured on TCPS; these observations were made with phase contrast and scanning electron microscopy. Keratinocytes of human and rat origin were also cultured on the closed top layers (of the 55 PEO/45 PBT composition) provided with porous underlayers of 55 PEO/45 PBT, 60 PEO/40 PBT and poly-L-lactic acid with a molecular weight of 104 kD and in the porous underlayers with 40 PEO/60 PBT, 55 PEO/45 PBT, 60 PEO/40 PBT and poly-L-lactide of molecular weight 104 kD composition. The differences between these biomaterials and TCPS were likewise statistically not significant.

Artificial ageing

The materials from which the artificial skins according to the invention were produced were treated in accordance with the Homsy artificial ageing method (C. A. Homsy, Bio-compatibility in selection of materials for implantation, J. Biomed. Mater. Res. (1970), pp. 341-356). Films of the materials to be used were heated in a pseudo-extracellular fluid (PECF) for 48 hours at 115° C. The PECFs of the various materials were then made up to complete media (D. Bakker, et al., Biocompatibility of six elastomers in vitro, J. Biomed. Mater. Res., 22 (1988), pp. 423-439). These media were added to three-day-old cultures of keratinocytes and fibroblasts of human and rat origin. Films of poly-L-lactic acid, the two Polyactive materials (i.e. 55 PEO/45 PBT and 40 PEO/60 PBT), two positive controls and one negative control were also examined in the ageing tests. The positive controls used were polyethylene terephthalate (Melinex) and standard PECF. The negative control used was polyvinyl chloride (PVC).

In the "artificial ageing" tests the morphological occurrence and the growth of the cells which were cultured in the media derived from poly-L-lactic acid or the Polyactive materials were found to be virtually the same as those of the cells which were cultured in the positive control media. Both the keratinocytes and the fibroblasts grew to confluence within 8 days. However, when media derived from PVC were used cell death occurred within 2 culture days.

Water vapour permeability

The water vapour permeability of four closed Polyactive materials (i.e. 30 PEO/70 PBT, 40 PEO/60 PBT, 55 PEO/45 PBT and 60 PEO/40 PBT) with thicknesses of 100, 200, 300 and 400 microns were determined gravimetrically using the "inverse cup" method in comparison with three commercially available products (i.e. Cutinova, Omiderm and Opside). The tests showed that the water vapour permeability of the abovementioned films was independent of the film thickness. The table below shows the water vapour permeability of the Polyactive films having a thickness of 100 microns which were examined:

TABLE 1

| Polyactive materials | | Commercially available products: | |
|---|---|---|---|
| 30 PEO/70 PBT | 29.7 ± 1.7 | Cutinova | 30.5 ± 0.6 |
| 40 PEO/60 PBT | 32.4 ± 0.9 | Omiderm | 31.6 ± 1.3 |
| 55 PEO/45 PBT | 33.6 ± 1.5 | Opsite | 5.5 ± 0.6 |
| 60 PEO/40 PBT | 33.2 ± 2.0 | | |

The water vapour permeability was carried out in triplicate and with standard deviation (in $g \cdot m^{-2} \cdot h^{-1} \cdot kPa^{-1}$) at a temperature of 35° C. and a relative humidity of 35%.

The prior art subscribes to the view that a water vapour permeability of 22 is ideal and that the upper limit is 29 (M. F. Jonkman, Design of the poly (ether urethane) wound covering and measurement of the water vapor permeance, in Epidermal Woundhealing Between Moist and Dry, Thesis Univ. Groningen). It may be expected that any cultured layer of keratinocytes which may be present will lower the water vapour permeability of the artificial skin and the higher (compared with the ideal situation) water vapour permeability of the films examined (on which no keratinocytes were cultured) may therefore be regarded as an advantage.

EXAMPLE II

Use of the artificial skin according to the invention in vivo, but without cultured keratinocytes Three male 0.5-year-old Wistar rats (350 g) with a dorsal wound of total thickness were provided with a steam-sterilized cell-free Polyactive (55 PEO/45 PBT) artificial skin made up from a closed top layer of 50 μm and a porous underlayer with a thickness of 210 μm and a macroporosity of 45%. After a period of 2 weeks, wound contraction, exudate formation and re-epithelization were compared with those of control animals whose dorsal wound had not been provided with an artificial skin.

After the use of the artificial skin according to the invention on the abovementioned wounds, this skin adhered immediately to the wounds as a result of capillary action and no accumulation of exudate formed under the artificial skin. Ingrowth of fibrous tissue and capillary formation also took place. Macrophages and foreign body giant cells, both of which are involved in the breakdown by the body of substances foreign to the body, were detected at the surface of the artificial skin material. Re-epithelization from the wound corners on the artificial skin was visible macroscopically after 8 days. The wound contraction was appreciably less, compared with the control wounds (see FIG. 2).

EXAMPLE III

Use of the artificial skin according to the invention in vivo, with cultured keratinocyte cells Six male Wistar rats with a body weight of 350 g and with a dorsal wound of total thickness were provided with an artificial skin (55 PEO/45 PBT, made up from a closed layer of 75 microns and a porous underlayer with a thickness of 220 microns and a macroporosity of 48%) sterilized by gamma radiation. In contrast to Example II, in the present example a layer of keratinocytes was cultured (in accordance with the abovementioned Rheinwald and Green method) on the top layer. During this experiment it was found that the cultured keratinocytes were still alive in at least 4 rats at a time 8 days after applying the artificial skin to the wound.

The water vapour permeability of the artificial skin according to the invention, which, depending on the composition, was 29.7±1.7 to 33.6±1.5 $g.m^{-2}.h^{-1}.kPa^{-1}$ and was high compared with normal skin (25 $g.m^{-2}.h^{-1}.kPa^{-1}$) and the commercial product "Opsite" (5 $g.m^{-2}.h^{-1}.kPa^{-1}$) was found to be important in order to make possible an adequate supply of nutrients from the subdermis to the dermis on the top of the artificial skin according to the invention.

EXAMPLE IV

In order to gain an impression of the size of the molecules (nutrients, amino acids, hormones) which can be transported through the closed top layer of the artificial skin, the permeability for three markers which varied in molecular weight (MW): the dye Malachite Green (MW 1.1 kD), albumin (BSA; MW 66 kD) and Immunoglobulin G (IgG; MW 150 kD), was determined (in triplicate) in a dialysis experiment on closed, 100 micron-thick films of 30 PEO/70 PBT, 40 PEO/60 PBT, 55 PEO/45 PBT and 60 PEO/40 PBT composition. The presence of Malachite Green in the buffer solution against the dialysate was determined spectrophotometrically; the presence of BSA and IgG was determined by means of a protein determination and an Enzyme-Linked Immunosorbent Assay (ELISA) respectively. It can be seen from the table below that the diffusion of the three markers from the dialysate into the buffer solution takes place through all films investigated. In other words, the films investigated are permeable for substances having a MW of the order of at least 150 kD.

TABLE 2

| Polyactives | Malachite | Green | BSA | IgG |
|---|---|---|---|---|
| 30 PEO/70 PBT | + + | + + | | + |
| 40 PEO/60 PBT | + + | + + | | + + |
| 55 PEO/45 PBT | + + | + + | | * |
| 60 PEO/40 PBT | + + | + + | | + + |

+ + Balance between dialysate and buffer after a maximum of 4 hours' dialysis
+ Balance between dialysate and buffer after a maximum of 8 hours' dialysis
*Determination not carried out In the light of the molecular size of the nutrients for keratinocytes (varying from smaller than 1 kD for glycose, pyruvate, etc. to 24 kD for the hormone Epidermal Growth Factor), qualitatively the supply of the substances useful for the keratinocytes appears to be assured.

It is seen from D. Bakker, et al., Biocompatibility of a polyether urethane, polypropylene oxide and a polyether polyester copolymer. A qualitative and quantitative study in the rat middle ear, J. Biomed. Mater. Res., 24 (1990), pp. 489-515, that porous films of a chemical analogue of 55 PEO/45 PBT are broken down in the rat. From studies in humans on porous films (porosity 50%, one side virtually closed, pore diameter 38-106 microns, thickness 100 microns) of 55 PEO/45 PBT, which are used to replace the ear drum, it is seen that the material dissolves in about 6 months.

LEGEND

FIG. 1 Growth curves of keratinocytes which have been cultured on closed Polyactive films and on TCPS, which latter material is a routine cell culture substrate. Two Polyactive materials were used for these cultures, namely the 55 PEO/45 PBT and the 40 PEO/60 PBT materials.

A: the curves relate to skin keratinocytes from the back of a rat;
B: the curves relate to keratinocytes of human foreskin.

The days are shown on the abscissa and the number of cells (×1000) are shown on the ordinate.

FIG. 2 shows the wound contraction after use of an artificial skin, according to the invention, of 45 PEO/55 PBT and a dorsal wound not provided with an artificial skin, as stated in Example II. The days are shown on the abscissa and the wound surface area, as a percentage of the original wound, is shown on the ordinate.

What is claimed is:
1. Artificial skin, made up of
   (1) a water vapour-permeable, non-porous top layer having a thickness of 5-200 um and made of a segmented thermoplastic copolyester, consisting essentially of a multiplicity of recurring long-chain-ester-units and short-chain-ester-units, the long-chain-ester-units making up 30-70% by weight of the copolyester and being represented by the formula

—OLO—CO—R—CO—

and the short-chain-ester-units being represented by the formula

—OEO—CO—R—CO—

wherein
   L in the long-chain-unit represents a divalent group which remains after removal of the terminal hydroxyl groups from a poly(oxyethylene) glycol with an average molecular weight of 500-3000;
   R is a divalent group which remains after removing the carboxyl groups from a dicarboxylic acid with a molecular weight of at most 300; and
   E in the above mentioned short-chain-unit represents an alkylene group having 2-6 carbon atoms, and
   (2) a macroporous lower layer of a degradable, biocompatible (co)polymer material selected from the group consisting of polymers and copolymers having a thickness of 30-300 um, the diameter of the macropores having a value of 30-300 microns and the macroporosity being 30-80%.
2. Artificial skin according to claim 1, wherein the non-porous top layer and the macroporous lower layer are produced from the same material.
3. Artificial skin according to claim 2, wherein the non-porous top layer and the macroporous lower layer gradually merge into one another forming a single-layer film.
4. Artificial skin according to claim 3, wherein the film thickness of the single-layer film is 100-300 um, the macroporosity thereof is 30-80% and the diameter of the macropores is 30-250 um.
5. Artificial skin according to claim 1, wherein the poly(oxyethylene) glycol unit L has an average molecular weight of 750-1500.
6. Artificial skin according to claim 5, wherein the poly(oxyethylene) glycol unit L has an average molecular weight of about 1000.
7. Artificial skin according to claim 1, wherein R is essentially derived from terephthalic acid.
8. Artificial skin according to claim 1, wherein E represents an alkylene group selected from the group consisting of —$CH_2$—$CH_2$—and—$CH_2$—$CH_2$—$CH_2$—$CH_2$—.
9. Artificial skin according to claim 1, wherein the macroporous lower layer is produced from poly-L-lactic acid with a molecular weight of $(5-100)10^4$.
10. A method of using the artificial skin of claim 1, including the step of providing the non-porous top layer of the artificial skin with autologous epithelial cells.
11. A method according to claim 10, including the step of providing the non-porous top layer of the artificial skin with autologous keratinocytes.
12. A method of using the artificial skin of claim 1, including the step of providing the porous lower layer of the artificial skin with autologous fibroblasts.

* * * * *